United States Patent
Kubiak et al.

(10) Patent No.: US 9,818,021 B2
(45) Date of Patent: Nov. 14, 2017

(54) METHOD FOR DETERMINING A LOCAL REFRACTIVE POWER AND DEVICE THEREFOR

(71) Applicant: ISRA SURFACE VISION GMBH, Herten (DE)

(72) Inventors: Rolf Kubiak, Dortmund (DE); Christian Ripperda, Cologne (DE)

(73) Assignee: ISRA SURFACE VISION GMBH, Herten (DE)

( * ) Notice: Subject to any disclaimer, the term of this patent is extended or adjusted under 35 U.S.C. 154(b) by 0 days.

(21) Appl. No.: 14/886,408

(22) Filed: Oct. 19, 2015

(65) Prior Publication Data

US 2016/0109362 A1   Apr. 21, 2016

(30) Foreign Application Priority Data

Oct. 21, 2014  (DE) .................. 10 2014 115 331
Oct. 21, 2014  (DE) .................. 10 2014 115 336

(51) Int. Cl.
*G06K 1/00*   (2006.01)
*G06K 9/00*   (2006.01)
(Continued)

(52) U.S. Cl.
CPC ....... *G06K 9/00208* (2013.01); *G01N 21/455* (2013.01); *G01N 21/958* (2013.01); *G06T 7/0008* (2013.01); *G01N 2021/9586* (2013.01); *G06T 7/0004* (2013.01); *G06T 2207/10028* (2013.01)

(58) Field of Classification Search
None
See application file for complete search history.

(56) References Cited

U.S. PATENT DOCUMENTS 5,151,752 A * 9/1992 Oono ................. G01M 11/0228
356/124
5,491,550 A * 2/1996 Dabbs ................. G01B 9/0207
250/227.27

(Continued)

FOREIGN PATENT DOCUMENTS

DE        10217068      5/2004
DE     012004033526    2/2006
(Continued)

OTHER PUBLICATIONS

Denis Perard et al: "Three-Dimentional Measurement of Specular Free-From Surfaces With a Structured-Lighting. . . ."
(Continued)

*Primary Examiner* — Shervin Nakhjavan
(74) *Attorney, Agent, or Firm* — Michael J. Striker; Elizabeth C. Richter

(57) ABSTRACT

A method for determining a local refractive power in a volume element of a transparent object using a pattern includes observing the pattern through the transparent object by a first camera, determining, using the observed pattern, a three-dimensional (3-D) shape and position of a surface of a particular volume element of the transparent object facing the pattern and using the determined 3-D shape and surface position of the particular volume element, determining a local refractive power for the particular volume element.

10 Claims, 1 Drawing Sheet

(51) Int. Cl.
*G01N 21/45* (2006.01)
*G01N 21/958* (2006.01)
*G06T 7/00* (2017.01)

(56) References Cited

U.S. PATENT DOCUMENTS

| | | | | |
|---|---|---|---|---|
| 5,946,100 | A * | 8/1999 | Ishihara | G01B 11/026 356/608 |
| 6,317,201 | B1 * | 11/2001 | Heckmeier | G01N 21/43 356/128 |
| 6,373,978 | B1 * | 4/2002 | Ishihara | G01B 11/026 382/154 |
| 8,064,069 | B2 | 11/2011 | Wienand et al. | |
| 8,224,066 | B2 * | 7/2012 | Haeusler | G01B 11/25 382/154 |
| 8,488,112 | B2 * | 7/2013 | Jeannot | G01B 11/0625 356/517 |
| 2002/0123868 | A1 * | 9/2002 | Yajima | G06T 15/20 703/2 |
| 2002/0191193 | A1 * | 12/2002 | Smirnov | G01N 21/45 356/517 |
| 2006/0028727 | A1 * | 2/2006 | Moon | G03H 1/0011 359/569 |
| 2006/0098190 | A1 | 5/2006 | Miyake et al. | |
| 2010/0110429 | A1 * | 5/2010 | Simoni | G01N 21/4133 356/328 |
| 2013/0293726 | A1 | 11/2013 | Armstrong-Muntner et al. | |
| 2014/0327909 | A1 * | 11/2014 | Kall | G01N 21/554 356/327 |
| 2015/0049331 | A1 * | 2/2015 | Ri | G01B 11/2513 356/73 |
| 2015/0055126 | A1 | 2/2015 | Gueu et al. | |
| 2015/0309300 | A1 * | 10/2015 | Higaki | G02B 21/14 348/79 |

FOREIGN PATENT DOCUMENTS

| | | |
|---|---|---|
| DE | 102006015792 | 10/2007 |
| DE | 102008023599 | 12/2008 |
| DE | 102013105570 | 12/2014 |
| EP | 2101143 | 9/2009 |
| EP | 2637011 | 9/2013 |
| JP | 11148813 | 6/1999 |
| KR | 1020050088434 | 9/2005 |

OTHER PUBLICATIONS

Harding, Kevin G. & Svetkoff, Donald J. (Eds), SPIE vol. 3200277-786X, 1997, pp. 74-80. ISBN 978-08194256369.

United Nations Economic Commission for Europe (ECE) R43 Regulation, Aug. 29, 2012.

Markus C. Knauer et al.: "Measuring the Refractive Power With Deflectometry in Transmission" Jan. 1, 2008, XP055258550, url:http://www.dgao-proceedings.de/download/109.

* cited by examiner

State of the Art

METHOD FOR DETERMINING A LOCAL REFRACTIVE POWER AND DEVICE THEREFOR

CROSS-REFERENCE TO A RELATED APPLICATION

The invention described and claimed hereinbelow is also described in German Patent Application DE 10 2014 115 336.7, filed on Oct. 21, 2014, and in German Patent Application DE 10 2014 115 331.6, also filed on Oct. 21, 2014. The German Patent Applications, subject matters of which are incorporated herein by reference, provide the basis for a claim of priority of invention under 35 U.S.C. 119(a)-(d).

BACKGROUND OF THE INVENTION

The present invention relates to a method for determining a local refractive power in a volume element of a transparent object using a pattern, which is observed through the transparent object by a camera. The invention furthermore relates to a device therefor.

For the quality inspection of transparent objects, e.g., glass panes for automobiles, the optical distortion is often measured using the device shown in FIG. 1. The optical distortion is converted to a local refractive power. In the known method mentioned in the United Nations Economic Commission for Europe (ECE) R43 Regulation, a projector 1 is used. The projector 1 projects a predefined pattern through a transparent object (e.g. a windshield) onto a projection wall 3. The light from the projector 1 passing through the windshield 2 is observed there using electronic means or manually. The windshield 2 is often tested in the installed position.

Since the windshield 2 has a non-negligible extension, the known distance (propagation length) $R_1$ between the projector 1 and the windshield 2 as well as $R_2$ between the windshield 2 and the projection wall 3 apply only for the region of the windshield 2 that lies on the optical axis between the projector 1 and the projection wall 3. The volume elements of the windshield remote from the optical axis have a greater spacing distance from the projector 1 and the projection wall 3. According to the aforementioned regulation, it is therefore required that high-precision measurements of the refractive power be carried out only on the optical axis. This means that either the windshield 2 or the projector 1, with the projection wall 3, must be moved in order to investigate a larger region of the windshield. This is highly time-consuming with respect to the measuring time.

SUMMARY OF THE INVENTION

The present invention overcomes the shortcomings of known arts, such as those mentioned above.

The invention provides a simpler and more cost-effective method for carrying out a high-precision measurement of the local refractive power on a transparent object than known methods, and realizes a cost-effective device therefor.

In one embodiment, the invention provides a method in which the three-dimensional shape and position of the surface of the particular volume element of the transparent object facing a pattern is ascertained and is used to determine the local refractive power. As used herein, volume element should be understood to be a three-dimensional element or part of a transparent object, for example, en element or part extending from a front side to a back side of the transparent object. As such, each transparent object consists of one or more volume elements, for example, a plurality of volume elements.

The local refractive power is determined in order to detect and classify optical faults, which induce optical distortions, e.g., within the scope of an automatic quality inspection of the transparent object. To this end, the determined local refractive powers are automatically compared with required refractive powers. If these do not match or if discrepancies that are too great exist between the determined local refractive powers and the required refraction powers for the particular volume element or a selected region of the transparent object, an error is reported. For example, an error associated with an object may be optically and/or acoustically indicated and/or the particular object is removed from the production process. To do so, the invention relies on means for determining such an error in a form of a computer device, such as a processor or electronic controller, which includes or is coupled to a means for generating an optical or acoustic indication, such as a loudspeaker. The removal of the object for which an error is reported can be facilitated, for example, by a picker arm or a branching in the belt conveyor, in communication with the processor or electronic controller. Alternatively, the removal may be controlled by a separate controller that is in communication with the above-mentioned processor or electronic controller.

In this connection, the local refractive power is understood to be the refractive power in the particular volume element of the object, which results from the particular curvatures of the surfaces of the particular volume element, the nature of the volume element and the refractive index (optical material property of the object), and is the reciprocal of the (local) focal length. The local refractive power is determined in any direction (optical axis), e.g., a direction which is required in the particular quality inspection, for example, the look-through direction through a windshield in the installed position.

In an embodiment, the three-dimensional shape of the surface and position relative to the particular volume element is determined by deflectometry with the aid of a camera. As an alternative, the three-dimensional shape and position of the surface can be determined by methods using reference marks, by purely mechanical, tactile measurements, or by a measurement of diffusively reflective surfaces via triangulation.

The inventive method is based on the finding that, when the three-dimensional geometric shape of the transparent and reflective object can be measured, it is advantageous to use these shape data to correct the refractive-value measurement in transmission. If the shape of the object is known, corresponding geometric corrections can be carried out. It is not absolutely necessary to carry out measurements of the refractive power for all volume elements on the optical axis. For the volume elements which do not lie on the optical axis in the above-described refractive-power determination, it is possible, given that the three-dimensional shape and position of the particular volume element of the object is known, to carry out a correction of the refractive power corresponding to the distance from the optical axis or corresponding to the curvature of the surface. This shortens the measuring time considerably and simultaneously increases the accuracy of the measurement, since the correct propagation length can be used. In addition, the method according to the invention therefore has greater reliability of the process. Furthermore, less space is required.

Given that the shape of the surface of the transparent object and the position of the individual volume elements are known, real coordinates can be assigned to these volume elements.

It is also advantageous that optical effects are measured, which are caused both by the large-surface-area shape of the object and by local deformations on the surface or in the volume of the object. According to the invention, when the three-dimensional overall shape (topography of the individual volume elements and the position thereof) of the object is known, the device can deduct global effects caused by the overall shape of the object. In other words, the refractive power of each volume element can be split into a portion caused by the global overall shape of the object and a portion for which only optical effects caused by local deformations (e.g. defects on the surface or in the volume) are significant. It is therefore possible, using the present invention, to separate large-surface-area and local optical effects.

The determination of the three-dimensional shape of the surface of the transparent object is carried out before the refractive-power measurement in transmission or simultaneously with this measurement.

In addition, the measuring results of the transmission optics, i.e., the ascertained refractive powers, are presented in a manner corrected for perspective, since the shape of the surface of the transparent object is known.

In an embodiment, a dynamic lattice is used to generate the pattern. This lattice generates different patterns for the refractive-power determination, for example, for different requirements, e.g., from customers, with respect to the quality inspection. The dynamic lattice electronically generates patterns which are suitable for the particular purpose of the measurement. The local refractive power is determined for each volume element on the basis of the local distortion of the pattern, which is considered in transmission.

When a dynamic lattice is used, a separate measurement must be carried out for each pattern, wherein the measurements are carried out in temporal succession. In an embodiment, different patterns can be color-coded and/or coded with respect to the polarization thereof, thereby allowing projection and measurement to take place simultaneously, which saves even more time. For example, three different lattices can be generated using three photodiodes (red, yellow, blue). This makes it possible to measure these three lattices simultaneously. The camera capturing the transmission images of the lattice can distinguish between the different lattices by a color and/or polarization filter.

In an embodiment, the three-dimensional overall shape of the surface of the transparent object facing the pattern is determined by combining the three-dimensional shapes of the surfaces of all volume elements. The overall shape of the surface of the transparent object is therefore composed of the individual shapes of the volume elements with consideration for the position of the particular volume element. In the case of a relatively large transparent object and/or relatively great curvatures in the surface of the object, a plurality of cameras is required in order to ascertain the overall shape of the transparent object, wherein each camera observes a portion of the transparent object.

It is furthermore advantageous that, since the three-dimensional overall shape of the surface of the transparent object is known, the curvatures of this surface and, therefore, the refractive powers of the transparent object with respect to the various viewing angles are known. The optics of the glass pane, which are based solely on the shape of the object as determined by the design, can therefore be calculated.

In an embodiment, the three-dimensional overall shape of the surface of the transparent object facing the pattern is compared with CAD data on the transparent object and, on the basis thereof, a visual range to be selected for the determination of the local refractive power is ascertained. Such a visual range (field of view) is sometimes required for the inspection of transparent objects, since it is often not the entire transparent object that is significant for the quality inspection, but rather merely one special region of the object, which is usually defined in the particular requirement.

The aforementioned problem is furthermore solved by a device for determining a local refractive power in a volume element of a transparent object, wherein the device is designed to determine the local refractive power with the aid of a predefined pattern, which can be observed through the transparent object by means of a camera, and to determine the three-dimensional shape and position of the surface of the particular volume element of the transparent object facing the pattern (e.g. in reflection) and use this to determine the local refractive power.

As explained above, the device is used within the scope of the automatic quality inspection of a transparent object.

The device according to the invention has the advantages mentioned above with respect to the method according to the invention. The device is designed to carry out the above-described method steps.

BRIEF DESCRIPTION OF THE DRAWINGS

Further features and advantages of the invention will become apparent from the description of embodiments that follows, with reference to the attached figures, wherein.

DETAILED DESCRIPTION OF THE PREFERRED EMBODIMENTS

The following is a detailed description of example embodiments of the invention depicted in the accompanying drawings. The example embodiments are presented in such detail as to clearly communicate the invention and are designed to make such embodiments obvious to a person of ordinary skill in the art. However, the amount of detail offered is not intended to limit the anticipated variations of embodiments; on the contrary, the intention is to cover all modifications, equivalents, and alternatives falling within the spirit and scope of the present invention, as defined by the appended claims.

Figure 1:
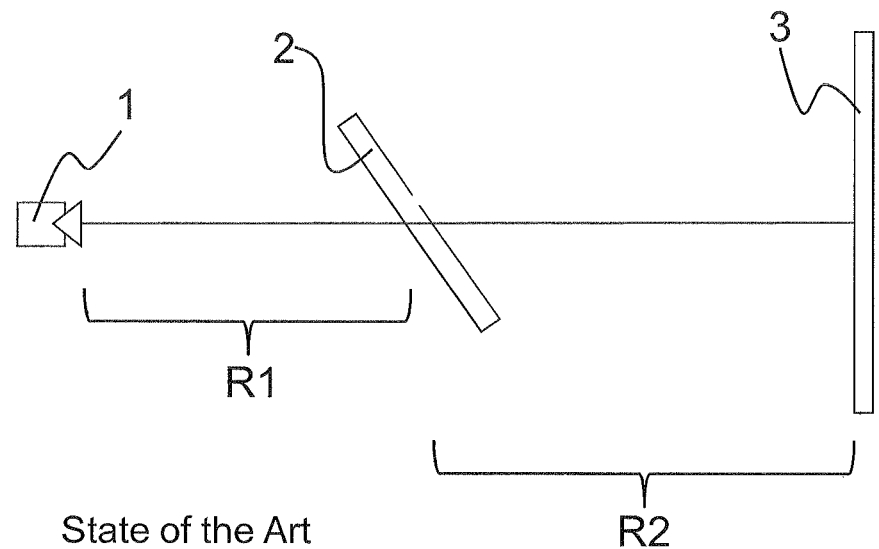
FIG. 1 presents a side view of a device for determining a local refractive power in a volume element of a transparent object according to the prior art.
Figure 2:
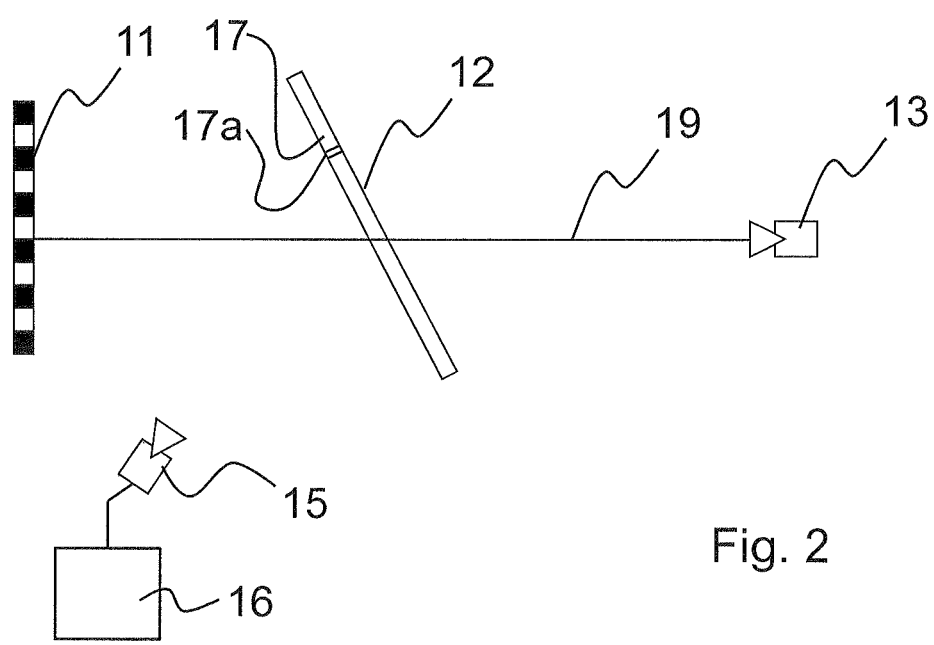
FIG. 2 presents a side view of a device according to the invention for determining a local refractive power in a volume element of a transparent object.

In the device depicted in FIG. 2, any type of pattern generated by a dynamic lattice 11 is observed by a first camera 13 through a transparent object in the form of a windshield 12 (comprising volume element 17a). On the basis thereof, local refractive powers for the volume elements 17a of the windshield 12 are determined in a manner known per se, and specifically also for the volume elements 17a located outside of the optical axis. Furthermore, a second camera 15 is provided, which is disposed on the same side of the windshield 12 as the dynamic lattice 11 and observes the light reflected by the windshield 12.

The shape of the surface 17 of the windshield 12 is simultaneously determined by deflectometry by the second camera 15. In so doing, the three-dimensional shape of the surface facing the pattern/lattice 11 is determined for each volume element 17a and the position of the particular volume element is determined. The shape of the surface 17 of the transparent object 12 is also considered in the determination of the local refractive power of the particular volume element 17a considered in the transmission measurement. The second camera 15 captures another image of the windshield 12 and then determines the shape of the surface 17 of the windshield 12 simultaneously.

Therefore, if the local refractive power was determined far outside the optical axis, it is possible to make corrections to the determined local refractive power for volume elements not lying on the optical axis 19, which corrections result from the shape of the surface 17 of the windshield 12 and the position of the volume element in the windshield. It is therefore not necessary to move either the windshield 12 or the first camera 13 with the dynamic lattice 11 during the measurement in order to determine the refractive power. As a result, the measuring time is considerably shortened and the accuracy of the determined refractive powers is increased.

The first camera 13 is used to measure optical effects on the basis of the distortion of the lattice 11. The optical effects are caused by the large-surface-area shape of the windshield 12 as well as by local deformations on the surface 17 or in the volume of the windshield 12. According to the invention, when the local three-dimensional shapes of the surface 17 of all volume elements are combined to form a three-dimensional overall shape of the surface 17 of the windshield 12, global effects caused by the large-surface-area shape of the object are deducted in the device.

Computer or electronic controller 16 determines the 3D shape of the surface 17 and the position of the volume element 17a. The computer or electronic controller 16 uses the 3D shape of the surface 17 and the position of the volume element 17a are used to determine the refractive power and to compare the refractive power to the predetermined refractive power. As a result, it is possible to indicate the optical effects caused by local deformations in the determination of the local refractive power. It is therefore possible, using the present invention, to separate large-surface-area and local optical effects.

Within the scope of a quality inspection of the transparent object, the refractive powers determined for the specified volume elements (e.g. of a visual range) are compared with required refractive powers of refractive power ranges. If the determined refractive powers do not match the required refractive powers or refractive power ranges, the particular transparent object does not meet the quality requirements and an error is signaled and/or the object is removed from the production process.

LIST OF REFERENCE NUMBERS 1 projector
2 transparent object
3 projection wall
R1 distance: protector-transparent object
R2 distance: transparent object-projection wall
11 dynamic lattice
12 windshield
13 first camera
15 second camera
16 computer
17 surface of the windshield
17a volume element As will be evident to persons skilled in the art, the foregoing detailed description and figures are presented as examples of the invention, and that variations are contemplated that do not depart from the fair scope of the teachings and descriptions set forth in this disclosure. The foregoing is not intended to limit what has been invented, except to the extent that the following claims so limit that.

What is claimed is:

1. A method implemented by an electronic computer for determining a local refractive power in a volume element of a transparent object using a pattern, the method comprising the steps of:
   observing the pattern through the transparent object by a first camera;
   observing light reflected from the object by a second camera;
   using the observed pattern and the light reflected from the object, the electronic computer determining a three-dimensional (3-D) shape and position of a surface of a particular volume element of the transparent object facing the pattern by deflectometry; and
   in reliance upon the determined 3-D shape and surface position of the particular volume element, the electronic computer determining a local refractive power for the particular volume element.

2. The method according to claim 1, further comprising generating the pattern by use of a dynamic lattice.

3. The method according to claim 1, further comprising determining a three-dimensional (3-D) overall shape of the surface of the transparent object facing the pattern is determined by combining three-dimensional (3-D) shapes of all volume elements.

4. The method according to claim 3, further comprising comparing the 3-D overall shape with CAD data on the transparent object; and
   based on the comparing, determining a visual range to be selected for the determination of the local refractive power.

5. The method according to claim 1, further comprising comparing the local refractive to a required refractive indices or refractive power ranges.

6. A device for determining a local refractive power in a volume element of a transparent object using a predefined pattern, comprising:
   a first camera for capturing an image of the predefined pattern through the transparent object;
   a second camera for capturing light reflected from the transparent object;
   an electronic computer for determining a three-dimensional (3-D) shape and position of a surface of a particular volume element of the transparent object facing the pattern in reliance upon the image of the pattern reflected through the object and captured by the first camera and in reliance upon the reflected light captured by the second camera, using deflectometry;
   wherein the electronic computer utilizes the 3-D shape and position of the surface of the particular volume element to determine a local refractive power for the particular volume element.

7. The device according to claim 6, further comprising a dynamic lattice for generating the predefined pattern.

8. The device according to claim 6, wherein the electronic computer determines a three-dimensional (3-D) overall shape of the surface of the transparent object facing the predefined pattern by combining three-dimensional (3-D) shapes of all volume elements comprising the transparent object.

9. The device according to claim 8, wherein the electronic computer compares the 3-D overall shape with CAD data on the transparent object and, on the basis thereof, ascertains a visual range to be selected for the determination of the local refractive power.

10. The device according to claim 6, wherein the electronic computer compares the local refractive power to a required refractive indices or refractive power ranges.

* * * * *